United States Patent [19]

Baker et al.

[11] Patent Number: 4,654,127
[45] Date of Patent: Mar. 31, 1987

[54] SELF-CALIBRATING SINGLE-USE SENSING DEVICE FOR CLINICAL CHEMISTRY AND METHOD OF USE

[75] Inventors: Richard W. Baker, Anoka; Roger L. Funk, Cedar, both of Minn.

[73] Assignee: SenTech Medical Corporation, Arden Hills, Minn.

[21] Appl. No.: 802,954

[22] Filed: Nov. 27, 1985

Related U.S. Application Data

[63] Continuation of Ser. No. 598,868, Apr. 11, 1984, abandoned.

[51] Int. Cl.⁴ .................. G01N 27/28; G01N 27/30
[52] U.S. Cl. ........................ 204/1 T; 204/401; 204/406; 204/409; 204/411; 204/412; 204/416; 422/68; 422/102
[58] Field of Search .......... 204/409, 401, 406, 411, 204/412, 416, 1 T; 73/1 R; 422/68, 98, 102; 436/68

[56] References Cited

U.S. PATENT DOCUMENTS

| | | | |
|---|---|---|---|
| 3,556,950 | 1/1971 | Dahms | 204/409 X |
| 3,698,238 | 10/1972 | Wall et al. | 73/53 |
| 3,884,640 | 5/1975 | Lock et al. | 436/68 X |
| 4,184,936 | 1/1980 | Paul et al. | 204/195 |
| 4,214,968 | 7/1980 | Battaglia et al. | 204/195 M |
| 4,233,029 | 11/1980 | Columbus | 23/230 R |
| 4,271,119 | 6/1981 | Columbus | 422/50 |
| 4,273,639 | 6/1981 | Gottermeier | 204/195 R |
| 4,283,262 | 8/1981 | Cormier et al. | 204/411 |
| 4,336,091 | 6/1982 | Gottermeier | 156/244.12 |
| 4,366,040 | 12/1982 | Marsoner et al. | 204/409 |
| 4,510,035 | 4/1985 | Seshimoto | 204/411 |

Primary Examiner—G. L. Kaplan
Attorney, Agent, or Firm—Kinney & Lange

[57] ABSTRACT

A single-use sensing device for a clinical chemistry analyzer system includes a carrier which supports a capillary passage. Species selective sensors are located within a test chamber portion of the capillary passage. A rotatable multichamber reservoir having a calibrant chamber for holding calibrant fluid and a sample chamber for containing a sample fluid is rotated first to a calibrant test position and then to a sample test position. In the calibrant test position, the calibrant chamber is connected to the inlet end of the capillary passage to draw calibrant fluid into the test chamber. In the sample test position, the sample chamber is connected to the inlet end to draw sample fluid into the test chamber and purge the calibrant fluid from the test chamber. A set of sensor readings are taken at each position, and concentration values are derived from the two sets of readings.

55 Claims, 15 Drawing Figures

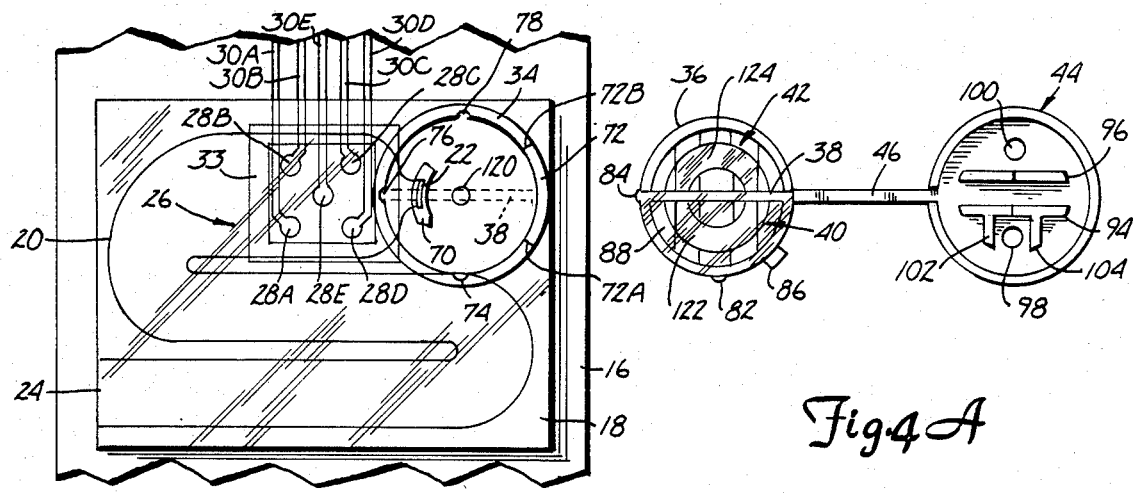
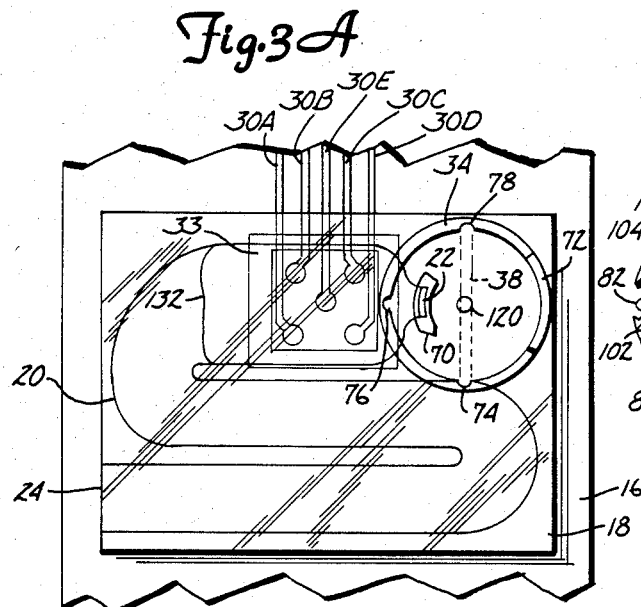
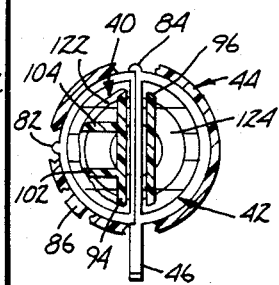
Fig.3A                Fig.4A
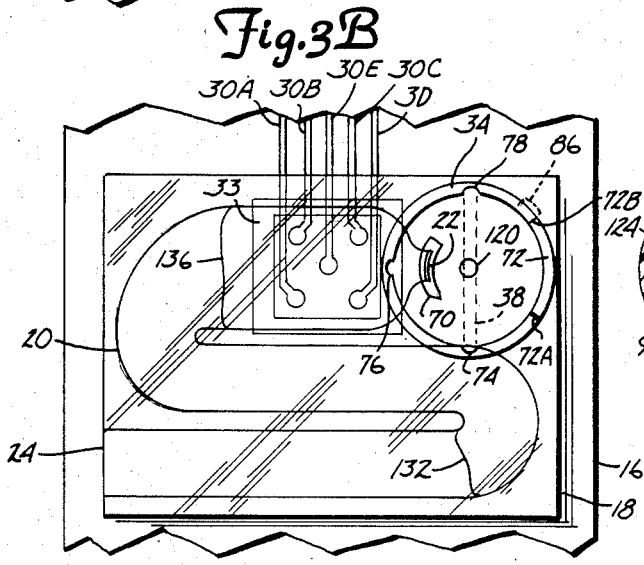
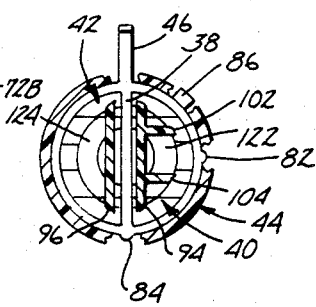
Fig.3B                Fig.4B
Fig.3C                Fig.4C

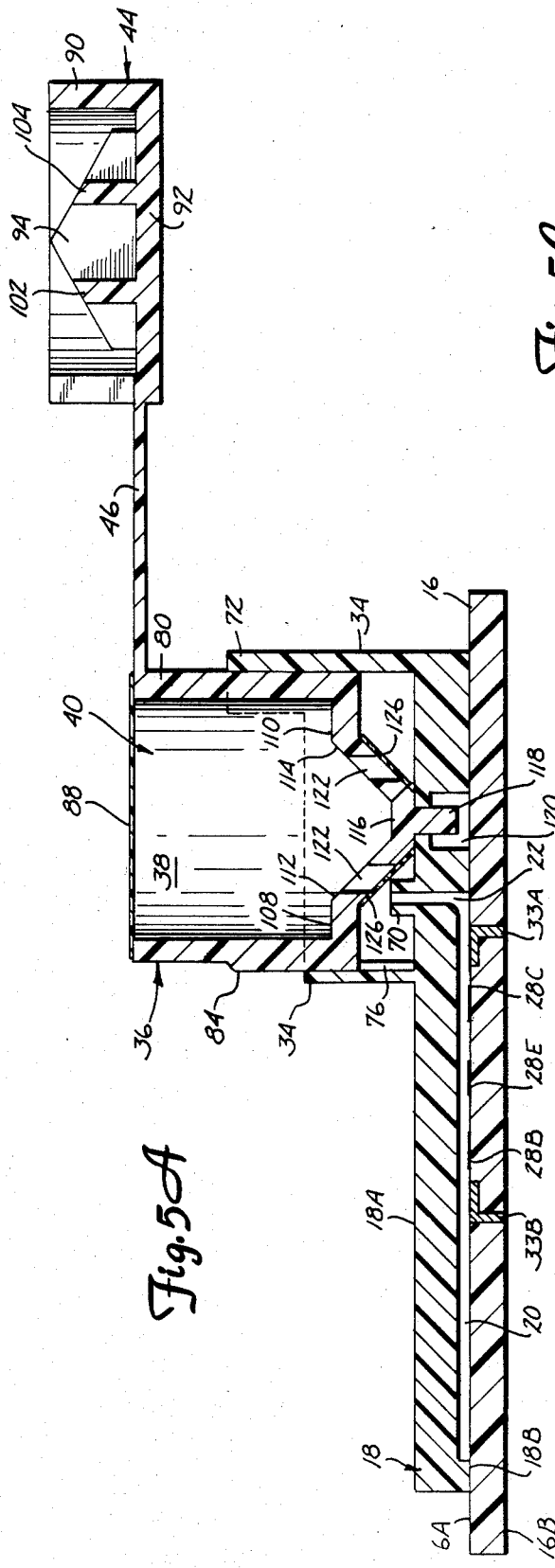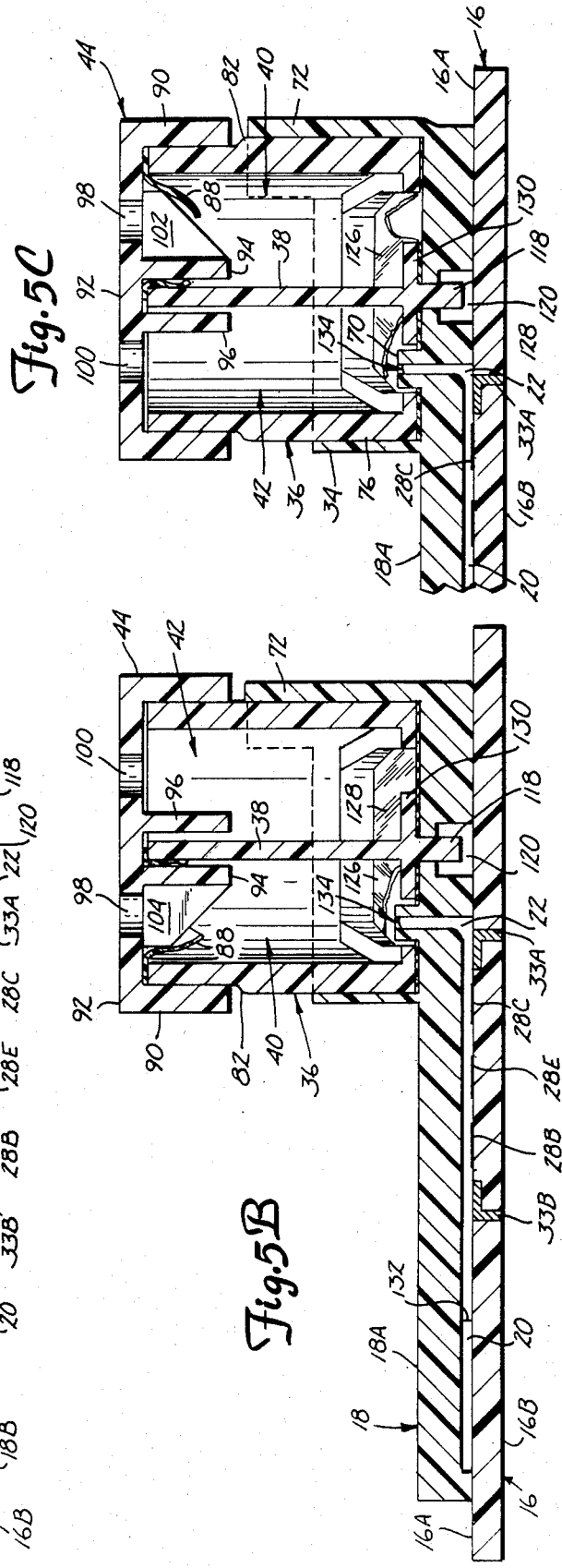

SELF-CALIBRATING SINGLE-USE SENSING DEVICE FOR CLINICAL CHEMISTRY AND METHOD OF USE

This is a continuation of application Ser. No. 598,868 Apr. 11, 1984 and now abandoned.

REFERENCE TO COPENDING APPLICATION

Reference is made to the following copending applications which are assigned to the same assignee as the present application: Ser. No. 550,360, filed Nov. 10, 1983 entitled "Clinical Chemistry Analyzer" by M. Knudson and W. Sembrowich; Ser. No. 550,361, filed Nov. 10, 1983 entitled "Multiple Species Group Disposable Sensing Device for Clinical Chemistry Analyzer" by M. Knudson, W. Sembrowich and S. Carlson and Ser. No. 550,313, filed Nov. 10, 1983 entitled "Disposable Single-Use Sensing Device For Clinical Chemistry Analyzer by R. Little and R. Laska.

BACKGROUND OF THE INVENTION

1. Field of the Invention

The present invention relates to medical devices. In particular, the present invention relates to clinical chemistry analyzers which are used for the measurement of medically significant substances in body fluids.

2. Description of the Prior Art

The increasing sophistication in the treatment of disease in recent years has led to the need for diagnostic instrumentation that will effectively gather accurate information on the patient before treatment begins. A critical component of this information gathering involves blood analysis for determining the presence and concentration of particular chemicals in the blood.

The methods by which chemical data are gathered for accurate medical diagnosis constitute a branch of medical science called clinical chemistry. Currently there are three major methods which are commonly used to measure the level of chemicals in blood or other body fluids. These methods are: optical, flame photometry, and ion selective electrodes.

The optical methods (which are sometimes referred to as spectrophotometric methods) operate on the principle that when specific reagents are mixed with a sample of the body fluid, a reaction takes place which allows the measurement of the chemical of interest by measuring the change in wavelength of light transmitted by the sample. The clinical chemistry analyzer systems which use an optical method have typically operated by either mixing the sample with a prepackaged amount of reagents or by allowing the mixing of the sample with the reagents through various tubing and mixing operations.

In flame photometry methods, the sample is consumed in a flame. The specific light produced by a given chemical of interest during the combustion process is used to determine the level of that chemical in the body fluid.

Ion selective electrode measurement methods use electrodes having membranes that selectively interact with chemical ions of interest. These methods involve a potentiometric, amperometric or other electrical measurement which is a function of the concentration of the ion of interest in the sample.

In the past, the clinical chemistry analyzers using optical, flame photometry or ion selective electrode methods have tended to be large in size, expensive, and complex to operate. Analyzers using optical techniques or ion selective electrodes have been expensive to acquire due to the complexity of the mechanical systems and the nature of the exacting measurement required. They have also needed trained operators to continually monitor and evaluate the measurements, have required exhaustive and frequent maintenance, and have required frequent calibration.

Analyzers using flame photometry have also required trained operators and an extremely high amount of maintenance. In addition, flame photometers have required a source of propane and an open flame, which is undesireable for safety reasons.

In general, only large medical institutions have been able to afford the purchase of clinical chemistry analyzers. Smaller hospitals, clinics and physician group practices usually have had to employ centralized hospital laboratories or commercial laboratories to do their chemical tests. These laboratories have grown substantially in the last decade with the increased emphasis on measurement of medically significant substances in the blood and other body fluids as a part of the physician's diagnosis prior to treatment.

In the past, basic blood chemistry tests have often been very time consuming. When a physician has required a basic blood test, a blood sample has been taken and sent to a laboratory for analysis. The results of the test in nonemergency cases has taken from one hour to several days. In the meantime, the patient may have left the clinic and then had to return later or be telephoned to consult with the physician on the results of the test. This procedure has been inconvenient and medically inefficient for both the physician and the patient.

There is a strong need for clinical chemistry instrumentation that can be readily available to all physicians who desire to conduct selected basic chemistry tests without delay and at a reasonable cost. This need extends to individual doctor's offices, physician group praactices, hospitals for bedside applications, operating and emergency rooms, cardiac and intensive care units, nursing homes, ambulances and emergency vehicles, and in centralized laboratories for immediate ("stat") use.

This need for improved clinical chemistry instrumentation, however, requires an analyzer which is less expensive to acquire, is easier to operate, requires less maintenance, eliminates the need for an open flame, eliminates the need for constant manual calibration and verification of measurements, reduces drift effects to a negligible level, eliminates need for handling of calibrated reagents, is portable enough to allow its use where required, and uses whole blood so that the time consuming step of centrifuging blood samples is eliminated, and requires very small volumes of blood for testing. The prior art clinical chemistry analyzers, however, have been unable to meet all of these requirements.

SUMMARY OF THE INVENTION

The present invention is an improved clinical chemistry analyzer system which utilizes single-use sensing devices in conjunction with an analyzer to determine concentration of selected chemical species in body fluids. The single-use sensing device receives and holds a sample of the body fluid, and is inserted into a receptacle of the analyzer when a measurement of the concentration of selected chemical species is to be made. Once the measurement has been made, the single-use sensing device is removed from the analyzer receptacle and can be discarded.

The single-use sensing device of the present invention includes a plurality of sensors which is positioned in a fixed spaced relationship in communication with a capillary passage. At least one of the sensors is a species sensor having a sensing portion which is capable of selective interaction with a selected chemical species, so that the species sensor exhibits a predetermined measurable characteristic which is a function of concentration of that selected chemical species.

The sensing device also includes means for sequentially connecting a source of a calibrant fluid and a source of the sample fluid to an inlet end of the capillary passage. The calibrant fluid is first drawn into the passage and into contact with a plurality of sensors. The analyzer performs a measurement of the selected chemical species in the calibrant fluid based upon the characteristics of the sensors in contact with the calibrant fluid.

When the source of sample fluid is connected to the inlet end of the capillary passage, the sample fluid is drawn into the capillary passage and purges the calibrant fluid from contact with the plurality of sensors. The analyzer then measures the concentration of the selected chemical species in the sample fluid. The analyzer uses the measurements of concentrations of the selected chemical species in the calibrant fluid and the sample fluid to provide a concentration value of the selected chemical species in the sample fluid.

In preferred embodiments of the present invention, the sources of calibrant fluid and sample fluid are first and second chambers which contain the calibrant and sample fluids, respectively. The first and second chambers are mounted for sequential relative movement with respect to the inlet end of the passage, so that first chamber and then the second chamber are moved into alignment with the inlet.

BRIEF DESCRIPTION OF THE DRAWINGS

FIGS. 3A-3C show top views of the support sleeve, capillary passage and sensors of the sensing device with the rotating cylinder (shown in phantom) at a start position, a calibrant test position, and sample test position, respectively.

FIGS. 4A, 4B and 4C are top views of the rotating cylinder (with portions of the cap removed for clarity in FIGS. 4B and 4C) at the start position, the calibrant test position, and the sample test position, respectively.

FIGS. 5A-5C are sectional views of the sensing device along Section 5—5 with the rotating cylinder at the start position, the calibrant test position, and the sample test position, respectively.

DETAILED DESCRIPTION OF THE PREFERRED EMBODIMENTS

Figure 1:
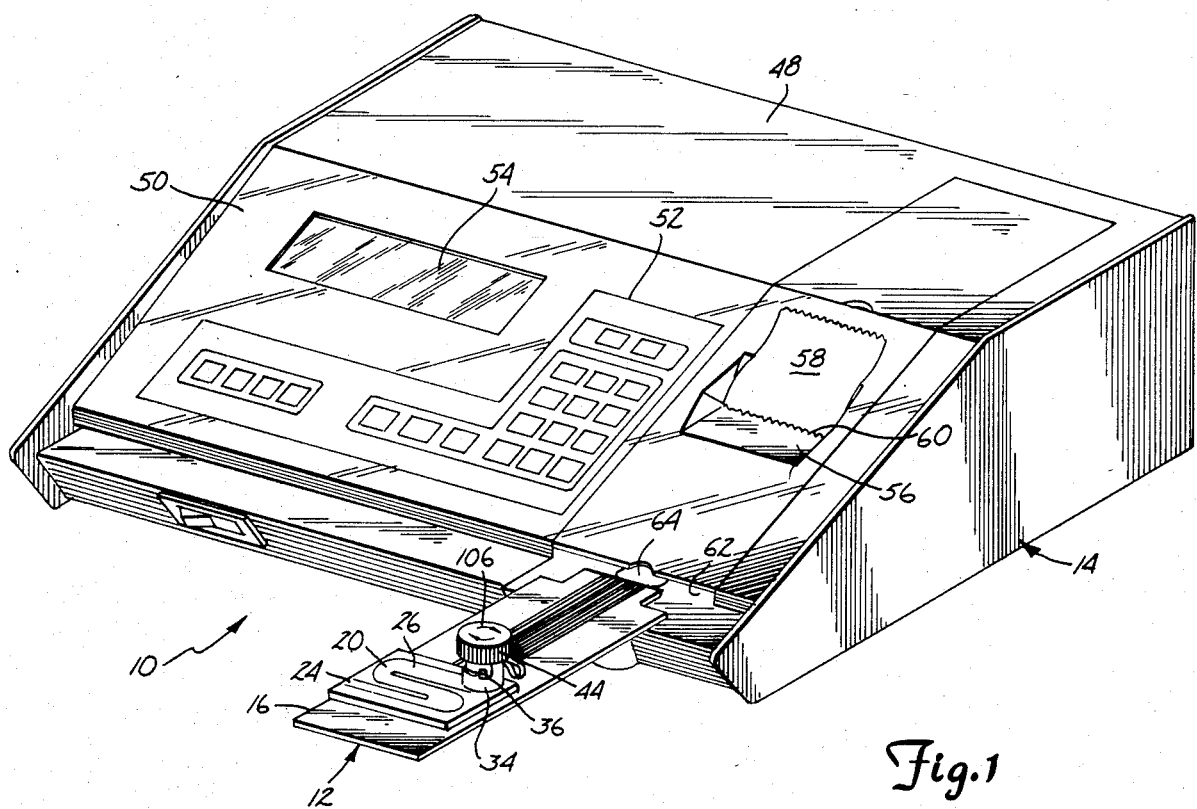
FIG. 1 is a perspective view of a preferred embodiment of an analyzer and a disposable sensing device of the present invention which form a clinical chemistry analyzer system.
Figure 2:
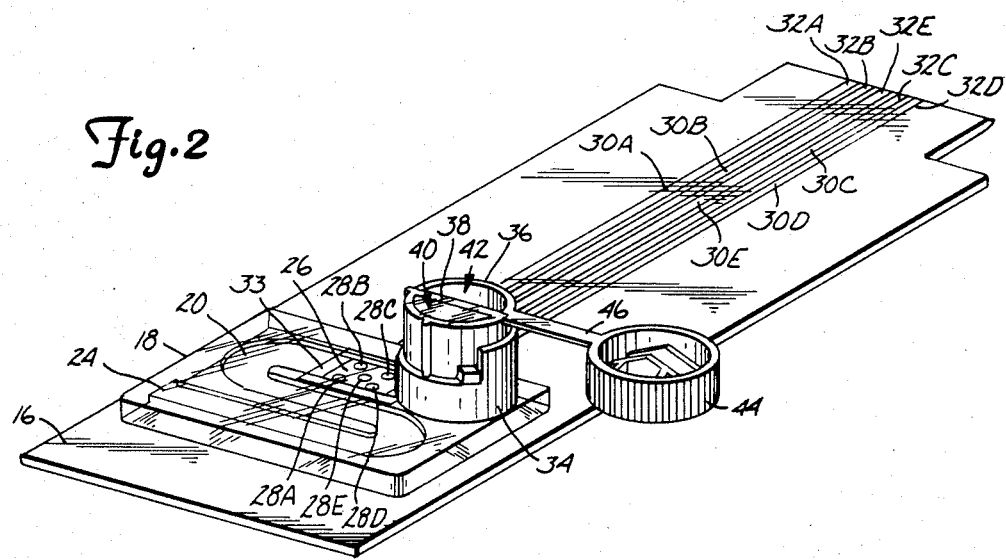
FIG. 2 is a perspective view of the disposable sensing device.

FIG. 1 shows a clinical chemistry analyzer system 10 which includes disposable single-use sensing device 12 and analyzer 14. System 10 is a compact, self-contained portable system which facilitates usage in a physician's office, an operating room, or a clinical chemistry laboratory to measure concentrations of chemicals in blood an other body fluids.

Sensing device 12 (which is shown in further detail in FIGS. 2–8) includes carrier 16 (which is in the form of a flat, generally rigid card) onto which plate 18 is bonded. In the embodiment illustrated in the Figures, plate 18 is a transparent plastic material, but it will be understood that in other embodiments plate 18 is not necessarily transparent. An S-shaped capillary passage 20 having an inlet 22 (FIGS. 3A-3C) and an outlet 24 is defined by carrier 16 and plate 18. Capillary passage 20 includes a test chamber or cavity 26 at an end nearest inlet 22. A plurality of sensors 28A-28E are supported by carrier 16 and exposed to the interior of test chamber 26 to interact with fluid contained within test chamber 26. Conductors 30A-30E extend between and interconnect sensors 28A-28E and electrical contacts 32A-32E, respectively. Electrical contacts 32A-32E are located near a front edge of carrier 16 to make electrical connection with the circuitry of analyzer 14. Insulating coating 16C (FIG. 8) covers the entire top surface 16A of carrier 16, except for over sensors 28A-28E and over contacts 32A-32E.

Heat transfer element 33 (FIGS. 3A-3C) is embedded in carrier 16 and is positioned to transfer heat to fluid within test chamber 26 so that measurements are made with the fluid at body temperature (37° C.).

Extending upward from top surface 18A of plate 18 and surrounding inlet 22 is cylindrical guide sleeve 34. Multi-chamber cylinder 36 is mounted for rotation within sleeve 34. Cylinder 36 has an interior wall 38 which divides the interior of cylinder 36 into calibrant chamber 40 which contains a calibrant fluid and sample chamber 42 which receives the sample of blood or other body fluid. The calibrant solution is factory sealed in chamber 40, and contains known concentrations of the species to be sensed by sensors 28A-28E. Cap 44, which is connected by web 46 to cylinder 36, is placed over the upper end of cylinder 36 after sample chamber 42 has received the body fluid sample.

Located on bottom surface 168 of carrier 16 is a bar code 47 (FIG. 8) which contains information on the type of sensing device (i.e. the particular species being sensed), sensor calibration data (including a slope value for each species selective sensor) and a lot number. The bar code and the information contained therein are discussed in further detail in the previously mentioned copending applications.

Housing 48 of analyzer 14 contains all of the electronic circuitry used to calculate concentrations of the chemical species of interest based upon signals from sensors 28A-28E of disposable sensing device 12. Analyzer 14 is preferably of a size which is suitable for desk or bench top use, or for use on a cart. Front panel 50 of analyzer 14 includes keyboard 52 and display 54, which allow an operator to interact and control the operation of analyzer 14. Analyzer 14 also includes printer 56, which provides a hard copy printout of the output of analyzer 14 (which preferably includes calculated concentrations and other derived values, warnings of abnormalities, time and data, lot number and/or serial number of sensing device 12, sample type and patient name or identification number). This printout is provided on print paper 58 which is fed out through opening 60.

Receptacle 62 of analyzer 14 is positioned to receive the forward end of sensing device 12. Within housing 48 there are electrical connectors positioned to connect contacts 32A-32E of sensing device 12 with the circuitry of analyzer 14. Also positioned adjacent to receptacle 62 is heater 64, which is contacted by heat transfer element 33. The heat produced by heater 64 is transferred by heat transfer element 33 to the fluid within test chamber 26 to heat the fluid to body temperature (37° C.). Also positioned adjacent to receptacle 62 is a bar code reader (not shown) for reading the information contained in the bar code when sensing device 12 is inserted into receptacle 62.

In system 10 of the present invention, sensors 28A-28E are calibrated immediately before the measurement of concentration of species in the sample. Just before device 12 is inserted into receptacle 62, the operator rotates cap 44 and cylinder 36 by 90° from a start position (illustrated in FIGS. 1, 2, 3A, 4A and 5A) to a calibrant test position (illustrated in FIGS. 3B, 4B and 5B) at which calibrant chamber 40 is connected to inlet 22 of capillary passage 20. The calibrant fluid contained within calibrant chamber 40 flows into test chamber 26, where it contacts sensors 28A-28E. When the flow of the calibrant fluid stops due to reduced hydraulic head and capillary action, and the calibrant fluid has been heated to body temperature, the calibrant test readings are made by analyzer 14. Once these readings have been made, the operator rotates cap 44 and cylinder 36 by 180° to a sample test position (illustrated in FIGS. 3C, 4C and 5C) at which sample chamber 42 is connected to inlet 22. The sample fluid flows into the chamber 26, and displaces the calibrant fluid into the narrower downstream portions of capillary passage 20. Thus test chamber 26 is purged of calibrant fluid by the sample fluid. The flow of the sample fluid into test chamber 24 stops, due to decreasing hydraulic head and capillary action, the sample fluid is heated to body temperature by heat transfer element 33, and the final measurements are made by analyzer 14. Based upon the sensor readings when calibrant fluid was in test chamber 26 and when the sample fluid was in test chamber 26, analyzer 14 derives concentrations and other values based upon those concentrations for each of the species of interest in the sample fluid.

With the present invention, therefore, the supply and control of flow of calibrant and sample fluids is achieved without degrading the fluids, and without the use of pumps or valves. In sensing device 12 of the present invention, both flow and control of the fluids are provided by a combination of liquid head and capillary forces.

The calibrant and sample fluids are aqueous. The calibrant fluid is typically a weak salt solution which flows essentially the same as pure water. The sample fluid (which is typically whole blood) is more viscous than water. It is also somewhat thixotropic. This means that it acts more viscous when flowing slowly than when flowing rapidly.

In the present invention, the amounts of fluid to be used typically are very small (e.g. about 100 to 200 microliters). The flow channels (particularly inlet 22 and capillary passage 20) must also be small to accommodate these small fluid volumes. The fluid flow, therefore, will always be laminar (viscous) in nature.

The main characteristic of viscous flow is that all the drag, against the flow of the fluid, is imposed at and by the wall of the channel and is transmitted to the fluid not near the wall by the fluid's viscosity. This means that a fluid with viscous flow will normally have a velocity profile which is a maximum at the center of the channel and substantially zero at the wall.

Liquid head is easy to understand: a liquid will flow out an opening in the bottom of a reservoir because of the pressure exerted by the liquid in the reservoir. The pressure provided by the liquid depends upon the liquid density and the height of the liquid in the reservoir.

Capillary force exists where a liquid and a gas are next to each other in a channel. This force is caused by the "attraction" of the liquid for the solid walls of the channel. The attraction is best understood as wetting ability of the liquid for the particular solid which forms the walls.

A liquid which wets a solid, such as pure water will wet clean glass, will exhibit a positive capillary force. This means the capillary force will tend to pull the liquid in the direction of the gas-liquid interface.

A liquid which does not wet a given solid (such as pure water will not wet polytetrafluoroethylene or greasy glass) will have a negative capillary force. In that case, the capillary force tends to push the liquid away from the gas-liquid interface.

Since the capillary force is exerted at the wall of the channel, the amount of force depends upon the circumference of the channel and the wetting ability of the liquid for the walls of the channel. The pressure is equal to the force divided by the cross-sectional area of the channel. In other words, the capillary pressure depends upon the ratio between the circumference of the channel and its cross-sectional area. The higher the ratio of circumference to area (such as is provided by a smaller channel), the higher the capillary pressure.

The use of capillary force as a pumping force tends to directly counteract the drag imposed by viscous forces and the effect of viscous forces on the velocity profile. The capillary force, which provides "pull" at the wall, counteracts the viscosity which imposes drag at the wall.

The operation of sensing device 12 of the present invention is decribed in further detail in FIGS. 3A-3C, 4A-4C amd 5A-5C. FIGS. 3A, 4A and 5A illustrate the relative position of plate 18, sleeve 34, cylinder 36 and cap 44 at the "start" position immediately before the sample fluid is deposited in sample chamber 42. FIGS. 3A and 4A are side-by-side and the angular orientation of cylinder 36 with respect to sleeve 34 is shown by FIGS. 3A and 4A.

FIGS. 3B, 4B and 5B illustrate the relative positions of plate 18, sleeve 34 and cylinder 36 at the "calibrant test" position during measurements of the concentrations in the calibrant fluid. FIGS. 3B and 4B are side-by-side, and show the angular orientation of cylinder 36 with respect to sleeve 34. In FIG. 4B, cap 44 has been broken away to show the interior of cylinder 36.

FIGS. 3C, 4C and 5C illustrate the relative position of cylinder 36 with respect to plate 18 and sleeve 34 at the "sample test" position when the chemical concentrations of the species of interest in the sample fluid are being measured. Once again, in FIG. 4C, cap 44 is partially broken away to reveal the interior of cylinder 36.

In this preferred embodiment, capillary passage 20 is formed between top surface 16A of carrier 16 and bottom surface 18B of plate 18 in the form of a channel in lower surface 18B of plate 18. In other embodiments, of course, capillary passage 20 can be formed by a channel in top surface 16A of plate 16.

Inlet 22 is an orifice in plow 70, which projects upward from top surface 18A of plate 18. Outlet 24 is located at the edge of plate 18. Capillary passage 20 is an S-shaped passage, with the upstream end of passage 22 (which is connected to inlet 22) forming test cavity or chamber 26. Sensors 28A-28E are positioned within test chamber 26. The remainder of S-shaped capillary passage 20 is narrower than test chamber 26.

Heat transfer element 33 is a square ring which surrounds sensors 28A-28E and is inlaid in a channel 71 in top surface 16A of carrier 16. A pair of flanges 33A and 33B project downward through passages 71A and 71B in carrier 16 and are exposed at bottom surface 16B to contact heater 64. Heat transfer element 33 is preferably a metal such as copper coated on its top surface with an insulator 33C such as epoxy so that the metal is not directly in contact with the fluid in test chamber 26, and so that conductors 30A-30E can extend from sensors 28A-28E over heat transfer element 33 and over top surface 16A of carrier 16 to contacts 32A-32E.

In the preferred embodiment of the present invention illustrated in the Figures, sensors 28A-28D are species selective sensors, and sensor 28E is a reference sensor. Each species selective sensor 28A-28D has a coating which includes a polymer and an electroactive species. The polymer serves the functions of creating a membrane over the sensor active area and immobilizing the electroactive species next to the electrically conductive surface of sensors 28A-28D. The particular electroactive species of each sensor 28A-28D differs, depending upon the species to be sensed. Reference sensor 28E either has no coating at all, or has a coating which is not specific to the particular chemical species of interest. Reference sensor 28E provides a reference from which an electrical measurement can be made by analyzer 14. By measuring an electrical characteristic (for example electrical potential or current) between each of the species sensors 28A-28D and reference sensor 28E, a set of signals or "readings" which are a function of chemical concentration of the particular chemical species of interest being sensed by species sensors 28A-28D can be obtained. In the present invention, these measurements are made twice, first with the calibrant fluid, and then with the sample fluid. Based upon the two sets of readings and the slope calibration value read from the bar code, analyzer 14 calculates the concentration of each of the chemical species of interest in the sample fluid.

Sleeve 34 projects upward from top surface 18A of plate 18. In a preferred embodiment of the present invention, sleeve 34 and plate 18 are an integral molded plastic part. Raised wall 72 projects upward above the remainder of sleeve 34 to define a pair of stop shoulders 72A and 72B. Sleeve 34 also includes vertical grooves 74, 76 and 78 which provide positive definition of the start, calibrant test and sample test positions of cylinder 36. Cylinder 36 has a circular cylindrical wall 80 with a pair of vertical ribs 82 and 84 and a stop projection 86. Ribs 82 and 84 and stop 86 cooperate with grooves 74, 76 and 78 and raised wall 72 of sleeve 34 to define the three positions and the direction of rotation of cylinder 36.

Dividing wall 38 is a vertical wall which divides the interior of cylinder 36 into two chambers: calibrant chamber 40 and sample chamber 42. The upper end of calibrant chamber 40 is sealed by membrane 88. The calibrant fluid is placed within calibrant chamber 40 during manufacturing of device 12, and calibrant chamber 40 is sealed by membrane 88 to prevent any spilling or evaporation of the calibrant fluid prior to the use of sensing device 12.

Sample chamber 42 has an open upper end to allow the medical personnel to deposit blood or other body fluid into sample 42.

In the preferred embodiment illustrated in the Figures, cap 44 and cylinder 36 are an integral molded plastic unit connected by web 46. Cap 44 has a cylindrical side wall 90 (with a slightly larger inside diameter than the outside diameter of cylinder 36) and a circular top 92. A pair of parallel drive flanges 94 and 96 are positioned so that when cap 44 is placed over the upper end of cylinder 36, flange 94 extends into calibrant chamber 40 and flange 96 extends into sample chamber 42 on opposite sides of dividing wall 38. Flanges 94 and 96 impart rotational force from cap 44 to cylinder 36 as cap 44 is rotated from the start position illustrated in FIGS. 3A, 4A and 5A to the calibrant test position shown in FIGS. 3B, 4B and 5B, and later to the sample test position illustrated in FIGS. 3C, 4C and 5C.

Cap 44 (which is also shown in perspective in FIG. 6) has a pair of vent holes 98 and 100 which overlie calibrant and sample chambers 40 and 42, respectively, when cap 44 is placed over cylinder 36. Drive flange 94 and gussets 102 and 104 (which are positioned on opposite sides of vent hole 98) are pointed to form a piercing blade which ruptures membrane 88 when cap 44 is placed over the upper end of cylinder 36.

Cylindrical wall 90 of cap 44 preferably has a knurled or grooved outer surface to aid the medical personnel in gripping and turning cap 44 and cylinder 36. Top 92 of cap 44 also preferably includes a pair of arrow indicators 106 (FIG. 1) which indicate to the operator the direction of rotation of cap 44 and cylinder 36.

Figure 7A:
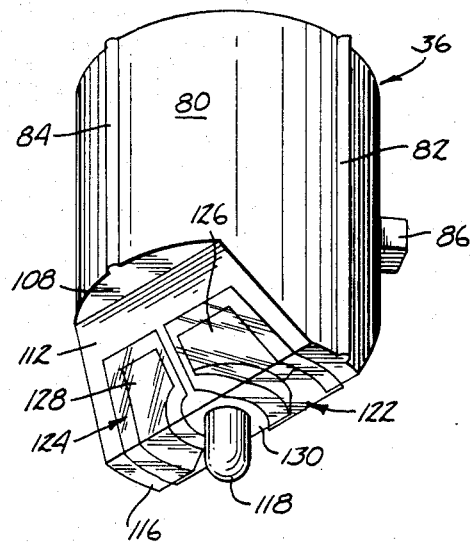
FIGS. 7A and 7B are perspective views, generally from the bottom, of the rotating cylinder.
Figure 7B:
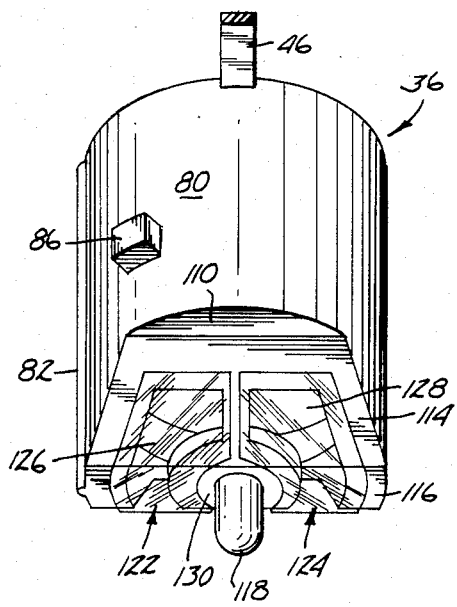
Figure 6:
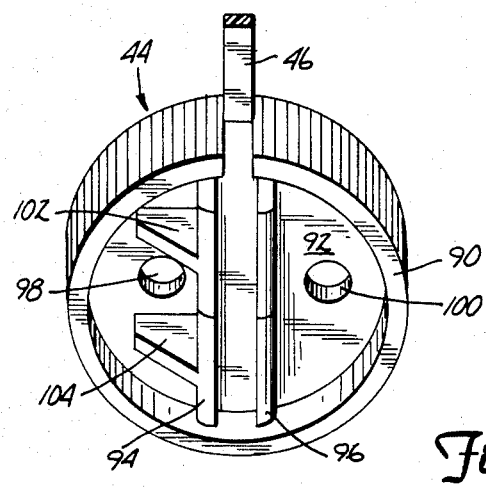
FIG. 6 is a perspective view, generally from the bottom, of the cap.
Figure 8:
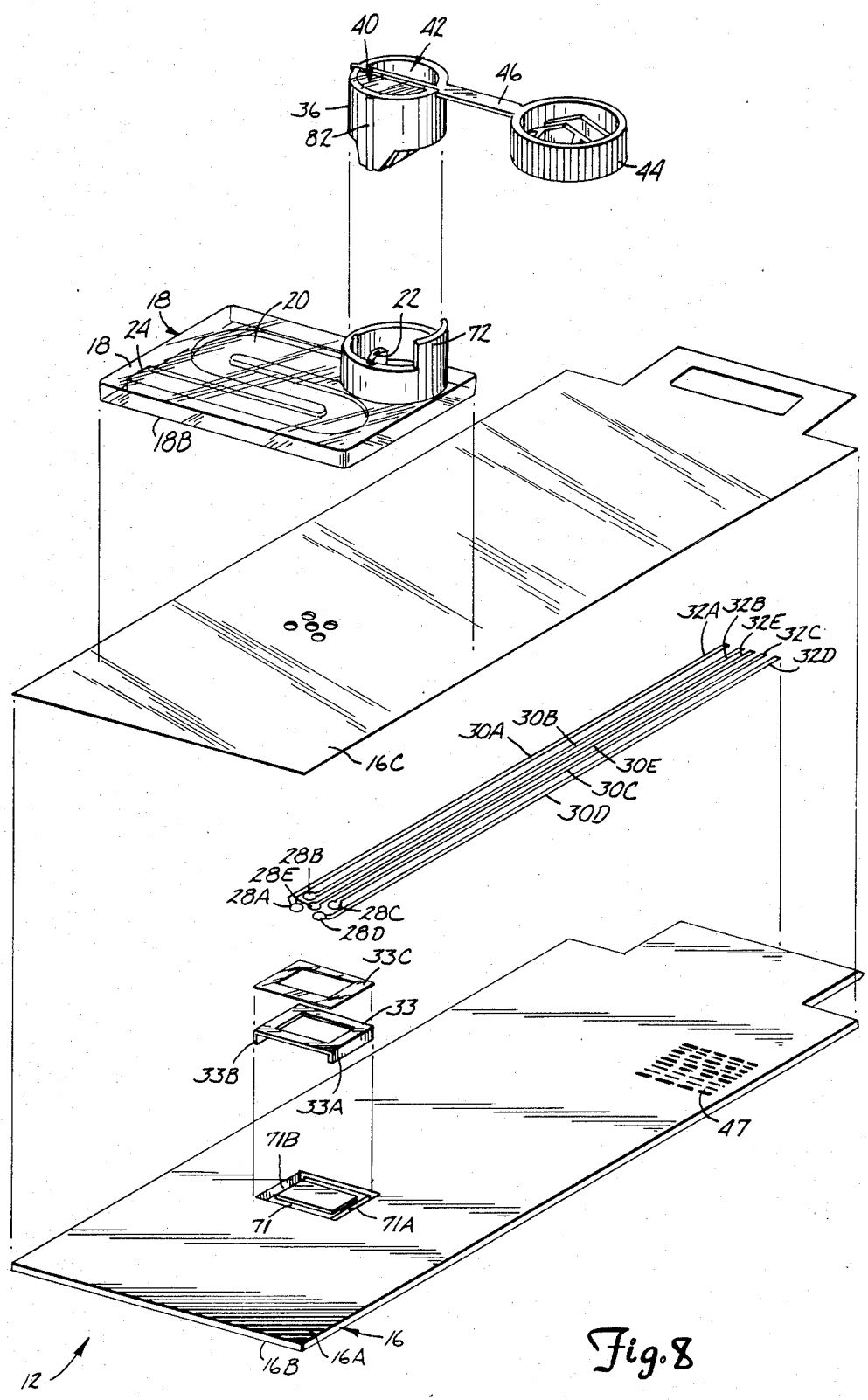
FIG. 8 is an exploded perspective view of the sensing device.

As best shown in FIGS. 7A and 7B, the bottom of cylinder 36 has a partially pyramidal or "V" shape formed by a pair of inwardly projecting flanges or shoulders 108 and 110, a pair of inclined walls 112 and 114 and end wall 116. Pilot pin 118 extends axially downward from lower end wall 116, and is captured within opening 120 of plate 18 to define an axis of rotation of cylinder 36.

Shoulders 108 and 110 lie in a common plane which is generally perpendicular to the axis of cylinder 36. Sholders 108 and 110 extend longitudinally in a direction perpendicular to dividing wall 38.

Inclined walls 112 and 114 are connected at their upper ends to shoulders 108 and 110, respectively. At their lower ends, walls 112 and 114 are connected to end wall 116. Each wall 112 and 114 is generally perpendicular to dividing wall 38.

End wall 116 is intersected by and is perpendicular to the central axis of cylinder 36. End wall 116 lies in a plane perpendicular to the central axis of cylinder 36 and extends in a longitudinal direction which is perpendicular to dividing wall 38.

Formed in inclined walls 112 and 114 and end wall 116 are a pair of arcuate openings 122 and 124 which communicate with chambers 40 and 42, respectively. Openings 122 and 124 divide inclined walls 112 and 114 and end wall 116 to create a central island 130 supported by dividing wall 38 and from which pilot pin 118 projects downward.

Membrane 126 covers opening 122 to seal the lower end of calibrant chamber 40. Similarly, membrane 128 covers opening 124 to seal the lower end of sample chamber 42. Membranes 126 and 128 (which are preferably inert polymer films) generally conform to the pyramidal or "V" shaped profile defined by inclined walls 112 and 114 and end wall 116.

In the start position shown in FIGS. 3A, 4A and 5A, cap 44 is open and cylinder 36 is positioned within sleeve 34 so that rib 82 is positioned in groove 74; rib 84 is positioned in groove 76; and stop projection 86 is positioned adjacent shoulder 72A. In this position, dividing wall 38 is located over plow 70 and, due to the profile of the bottom of cylinder 36, plow 70 is not in engagement with either membrane 126 or membrane 128.

When the sample fluid has been deposited in chamber 42 and testing is ready to begin, the operator provides an input to analyzer 14 through keyboard 52. Analyzer 14 then displays a prompt message, through display 54 which instructs the operator to close cap 44 over cylinder 36, to rotate cap 44 to the calibrant test position (illustrated in FIGS. 3B, 4B and 5B) and to insert device 12 into receptacle 62.

As cap 44 is placed over the top end of cylinder 36, flange 94 and gussets 102 and 104 rupture top membrane 88 to expose the interior of calibrant chamber 40 to the atmosphere through vent hole 98. Vent hole 100 provides exposure of sample chamber 422 to atmospheric pressure. No movement of fluid occurs, however, because the bottom ends of calibrant chamber 40 and sample chamber 42 are sealed by membranes 126 and 128, respectively.

Insertion of device 12 into receptacle 62 causes the bar code on the bottom of device 12 to be read and connects contacts 32A-32E to analyzer 14. It also brings heat transfer element 33 into contact with heater 66.

Rotation of cap 44 and cylinder 36 is possible in only one direction (clockwise) due to shoulder 72A and projection 86. The calibrant test position is positively defined by grooves 76 and 78. Rib 82 is positioned within groove 76, and rib 84 is positioned in groove 78 when cylinder 36 is in the calibrant test position.

As cylinder 36 is turned from the start position to the calibrant test position, the leading edge of plow 76 ruptures membrane 126 to insert inlet 22 (which is located within plow 70) into the calibrant fluid. The top end of plow 70 projects into calibrant chamber 40 to ensure fluid communication between inlet 22 and chamber 40.

The calibrant fluid within calibrant chamber 40 is drawn down through inlet 22 and into test chamber 26 of capillary passage 20 (as illustrated by the arrows in FIG. 5B. The calibrant fluid is drawn down by a combination of capillary force and hydraulic head, until calibrant chamber 40 is empty.

When calibrant chamber 40 is empty, the flow of calibrant fluid stops for two reasons. First, the hydraulic head is greatly reduced. Second, the capillary force exerted by the small orifice (inlet 22), which acts in a reverse direction, is greater than that exerted by the larger main capillary passage 20. This is because inlet 22 has a higher circumference-to-area ratio, and therefore exerts a greater capillary pressure than does test chamber 26. Put another way, forward gas-liquid interface 132 in test chamber 26 cannot provide enough "pull" to pull rearward gas-liquid interface 134 through the much smaller inlet orifice 22.

With flow stopped, calibrant fluid is heated to body temperature by heat transfer element 33. Readings are then made by analyzer 14, based upon the interaction of species selective sensors 28A-28D and reference sensor 28E with the calibrant fluid.

While calibrant testing is occurring, analyzer 14 displays a prompting message which requests entry of a patient identification number. The operator enters the patient identification number through keyboard 52.

Once the calibrant test readings have been completed, analyzer 14 displays a prompting message through display 54 instructing the operator to rotate cap 44 and cylinder 36 to the sample test position (FIGS. 3C, 4C and 5C). In the sample test position, rib 84 is positioned in groove 74 and stop 86 is adjacent shoulder 72B. This prevents any over-rotation of cylinder 36 beyond the sample test position.

As cap 44 and cylinder 36 are rotated from the calibrant test position through 180° to the sample test position, plow 70 tears open membrane 128 which seals the bottom of sample chamber 42, and inlet 22 is inserted into the sample fluid. This releases the capillary pressure imposed by inlet 22 (because inlet 22 is now under the sample fluid so that rearward liquid-gas interface 134 is no longer located at inlet 22). This allows the sample fluid to be drawn into capillary channel 20, thus purging the calibrant fluid from test chamber 26 and replacing it with sample fluid. The movement of sample fluid into test chamber 26 continues and calibrant sample fluid boundary 136 moves downstream until either the sample chamber 42 is empty and flow stops because rearward liquid-gas interface 134 is again located at inlet 22; or forward liquid-gas interface 132 reaches outlet 24 of capillary passage 20 (whereupon the flow stops because the capillary pressure provided by capillary passage 20 stops).

Once flow has stopped, the sample fluid is heated, and analyzer 14 takes a second set of measurements which are based upon the interaction of sensors 28A-28E with the sample fluid. When the measurements have been completed, analyzer 14 provides a prompting message which indicates to the operator that sensing device 12 can be removed from receptacle 16. Analyzer 14 calculates concentration values for each of the species of interest based upon the calibrant and sample sets of readings, and provides an output through display 54 and printer 56 which indicates the patient's identification number, and the measured concentrations and other values derived from those measured concentrations.

With the present invention, reliable sensing of concentrations of chemical species in very small samples is achieved. The operation of the system is independent of the size of the sample, as long as it is greater than a predetermined minimum amount such as 100 microliters.

The present invention provides calibration of the sensors immediately before measurement, and provides results which are available within a matter of several minutes. This calibration is achieved without requiring any handling of calibrant fluids, or any other manual action other than the rotation of the cap 44 and cylinder 36 from the start position to the calibrant test position.

The present invention is also simple in construction and operation and therefore reliable as to both the accuracy of results provided and the ease of operation (and therefore the probability of correct operation).

In the present invention, the calibrant and sample fluids are caused to flow and to stop as necessary without the need for pumps or valves. Sensing device 12, therefore, has a minimum number of parts, and is capable of being manufactured on a large-scale, automated basis. This ensures the low cost, disposable nature of sensing device 12.

The present invention provides reliably consistent purging of the calibrant fluid from test chamber 26 by the sample fluid. This purging feature is achieved because the "pumping" pressure (which is determined by the geometry of capillary passage 20, is always the same; and because the flow is low enough that the thixotropic nature of the sample fluid (which is typically whole blood) tends to cause it to flow as a plug instead of a parabola.

In some cases, multiple calibrant tests prior to the sample test can be advantageous. The present invention is particularly well suited to these more complicated sets of calibrant tests, since multiple calibrant tests can be accommodated by dividing cylinder 36 into more than two chambers. In that case, each calibrant chamber is rotated in turn to inlet 22 and a corresponding set of calibrant test readings are taken. Thereafter, the sample chamber is rotated to inlet 22 and the sample test readings taken.

Although the present invention has been described with reference to preferred embodiments, workers skilled in the art will recognize that changes may be made in form and detail without departing from the spirit and scope of the invention.

For example, although the embodiment illustrated in the Figures show conductors 30A–30E and contacts 32A–32E on the top surface 16A of carrier 16, in other embodiments they are positioned on bottom surface 16B. In those embodiments, the electrode portions of sensors 28A–28E extend through carrier 16 to be exposed at bottom surface 16B. In still other embodiments contacts 30A–30E are not required, and contacts 32A–32E are the bottom surfaces of the electrode portions of sensors 28A–28E which are exposed at bottom surface 16B and are contacted directly by an array of spring loaded contacts positioned along the bottom side of receptacle 62.

What is claimed is:

1. A disposable single use sensing device for use with a clinical chemistry analyzer which determines a concentration of a selected chemical species in a sample fluid based upon sensor signals received at a receptacle, the sensing device comprising:
    a carrier;
    a calibrant chamber for containing a calibrant fluid;
    a sample chamber for containing the sample fluid;
    a capillary passage supported by the carrier and having an inlet and having an outlet which is open to ambient air;
    first rupturable seal means for sealing an end of the calibrant chamber;
    second rupturable seal means for sealing an end of the sample chamber;
    means for defining a start position in which neither the calibrant chamber nor the sample chamber is connected to the inlet, a calibrant test position in which the calibrant chamber is connected to the inlet, and a sample test position in which the sample chamber is connected to the inlet;
    means for rupturing the first seal means to permit the calibrant chamber to be connected to the inlet and rupturing the second seal means to permit the sample chamber to be connected to the inlet;
    mounting means for mounting the calibrant and sample chambers to permit sequential relative movement of the chambers with respect to the inlet of the capillary passage from the start position to one of the test positions to draw the fluid from one of the chambers into the capillary passage and then to the other of the test positions to draw the fluid from the other chamber into the capillary passage, the fluid being drawn at least in part by capillary action; and
    sensing means for sensing concentration of the chemical species, the sensing means being positioned in communication with the capillary passage to provide sensor signals which are a function of sensed concentrations of the chemical species in the calibrant fluid and in the sample fluid.

2. The sensing device of claim 1 wherein the capillary passage has a test chamber of a first circumference connected to the inlet and a downstream channel of a second smaller circumference connected between the test chamber and the outlet.

3. The sensing device of claim 2 wherein the sensing means is positioned in the test chamber.

4. The sensing device of claim 3 wherein the capillary passage is S-shaped.

5. The sensing device of claim 1 wherein the mounting means rotatably connects the calibrant chamber and the sample chamber with the carrier.

6. A sensing device comprising:
    a carrier;
    a calibrant chamber for containing a calibrant fluid;
    a sample chamber for containing a sample fluid;
    a capillary passage supported by the carrier and having an inlet and an outlet;
    mounting means for mounting the calibrant and sample chambers to permit sequential relative movement of the chambers with respect to the inlet of the capillary passage to draw the fluid from one of the chambers and then the fluid from the other chamber into the capillary passage;
    a rupturable seal at an end of each of the chambers;
    a plow containing the inlet of the capillary passage for rupturing each seal and extending into each chamber as relative movement brings that chamber into alignment with the inlet; and
    sensing means for sensing concentration of chemical species, the sensing means being positioned in communication with the capillary passage to provide sensor signals which are a function of sensed concentrations of the chemical species in the calibrant fluid and in the sample fluid.

7. A sensing device comprising:
    a carrier;
    a calibrant chamber for containing a calibrant fluid;
    a sample chamber for containing a sample fluid;
    a capillary passage supported by the carrier and having an inlet and an outlet;
    mounting means for mounting the calibrant and sample chambers to permit sequential relative movement of the chambers with respect to the inlet of the capillary passage to draw fluid from one of the chambers and then the fluid from the other chamber into the capillary passage, wherein the mounting means rotatably connects the calibrant chamber and the sample chamber with the carrier, wherein the mounting means includes a cylindrical guide sleeve supported by the carrier, and wherein the calibrant and sample chambers are within a cylinder which is rotatably mounted in the cylindrical guide sleeve; and sensing means for sensing concentration of chemical species, the sensing means being positioned in communication with the capillary passage to provide sensor signals which are a function of sensed concentrations of the chemical species in the calibrant fluid and in the sample fluid.

8. The sensing device of claim 7 and further comprising a rupturable top seal covering a top end of the calibrant chamber; and means for rupturing the top seal to expose the calibrant fluid to atmospheric pressure.

9. The sensing device of claim 8 and further comprising a cap for fitting over an upper end of the cylinder.

10. The sensing device of claim 9 wherein the cap has vent means for exposing sample fluid and body fluid within the chambers to atmospheric pressure.

11. The sensing device of claim 10 wherein the vent means comprises a vent hole in the cap positioned over each of the chambers.

12. The sensing device of claim 9 wherein the means for rupturing the seal at the top end is carried by the cap.

13. The sensing device of claim 9 wherein the cylinder includes a vertical dividing wall for dividing an interior of the cylinder into the calibrant and sample chambers.

14. The sensing device of claim 13 wherein the cap includes a first drive flange extending generally downward from an interior surface of the cap for engaging the dividing wall to transmit rotational force from the cap to the cylinder when the cap is rotated.

15. The sensing device of claim 14 wherein the cap further includes a second drive flange spaced from the first drive flange and extending downward from the interior surface of the cap for engaging the dividing wall to transmit rotational force from the cap to the cylinder.

16. The sensing device of claim 14 wherein the means for rupturing the top seal includes the first drive flange.

17. The sensing device of claim 16 wherein the means for rupturing the top seal further includes a plurality of gussets connected to the first drive flange, the gussets and first drive flange forming a downwardly pointed blade for rupturing the top seal.

18. The sensing device of claim 7 and further comprising means for defining a start position in which neither the calibrant chamber nor the sample chamber is aligned with the inlet, a calibrant test position in which the calibrant chamber is aligned with the inlet, and a sample test position in which the sample chamber is aligned with the inlet.

19. The sensing device of claim 18 and further comprising means for limiting rotation of the cylinder from the start position to a direction toward the calibrant test position.

20. The sensing device of claim 18 and further comprising:
a rupturable bottom seal at a bottom end of each chamber; and
a plow containing the inlet of the capillary passage for rupturing each bottom seal and extending into each chamber as rotation of the cylinder brings that chamber into alignment with the inlet.

21. The sensing device of claim 20 wherein the cylinder has a vertical dividing wall for dividing an interior of the cylinder into the calibrant and sample chambers, and has a generally V-shaped bottom which includes a pair of inclined walls which are generally perpendicular to the dividing wall.

22. The sensing device of claim 18 wherein the means for defining a start position, a calibrant test position and a sample test position comprises a plurality of circumferentially spaced detents.

23. A sensing device for sensing concentration of a chemical species, the sensing device comprising:
a capillary passage having an inlet and having an outlet which is open to ambient air;
a plurality of sensors positioned in fixed space relationship in communication with the capillary passage to produce sensor signals, wherein at least one of the sensors is a species sensor having a sensing portion which is capable of selective interaction with a selected chemical species so that the species sensor exhibits a predetermined measurable characteristic which is a function of concentration of that selected chemical species;
a first sealed chamber containing a calibrant fluid;
a second chamber for receiving a sample fluid;
means for sequentially connecting the first and second chambers to the inlet of the capillary passage to draw one of the fluids into the passage and into contact with the plurality of sensors, and then the other fluid into the capillary passage to purge the one fluid from contact with the plurality of sensors and bring the other fluid into contact with the plurality of sensors; said means for sequentially connecting being manually movable from a start position in which neither chamber is connected to the inlet, to a first test position in which one of the chambers is connected to the inlet, and then to a second test position in which the other chamber is connected to the inlet; and
means for rupturing a seal of the first sealed chamber to permit calibrant fluid to be drawn from the first sealed chamber into the passage.

24. The sensing device of claim 23 wherein the sources of calibrant fluid and sample fluid comprises a multichamber reservoir having a calibrant chamber for containing the calibrant fluid and a sample chamber for containing the sample fluid.

25. The sensing device of claim 24 wherein the means for sequentially connecting mounts the multichamber reservoir for relative movement with respect to the inlet of the capillary passage.

26. The sensing device of claim 25 wherein the multichamber reservoir is a cylindrical reservoir having a generally vertical axis and having a generally vertical dividing wall for dividing an interior of the reservoir into the calibrant and sample chambers.

27. The sensing device of claim 26 wherein the means for sequentially connecting comprises means for rotatably mounting the reservoir for rotation about the generally vertical axis, and means for applying force to the reservoir to rotate the reservoir about the vertical axis to sequentially bring a lower end of the calibrant chamber and a lower end of the sample chamber into connection with the inlet of the capillary passage.

28. The sensing device of claim 23 wherein the capillary passage has a test chamber of a first circumference connected to the inlet and a downstream channel of a second smaller circumference connected between the test chamber and the outlet.

29. The sensing device of claim 28 wherein the sensing means is positioned in the test chamber.

30. The sensing device of claim 29 wherein the capillary passage is S-shaped.

31. A sensing device for sensing concentration of a chemical species, the sensing device comprising:
- a capillary passage having an inlet;
- a plurality of sensors positioned in fixed space relationship in communication with the capillary passage to produce sensor signals, wherein at least one of the sensors is a species sensor having a sensing portion which is capable of selective interaction with a selected chemical species so that the species sensor exhibits a predetermined measurable characteristic which is a function of concentration of that selected chemical species;
- a source of a calibrant fluid;
- a source of a sample fluid; and
- means for sequentially connecting the source of a calibrant fluid and the source of a sample fluid to the inlet of the capillary passage to draw one of the fluids into the passage and into contact with the plurality of sensors, and then the other fluid into the capillary passage to purge the one fluid from contact with the plurality of sensors and bring the other fluid into contact with the plurality of sensors;
- wherein the sources of calibrant fluid and sample fluid comprises a multichamber reservoir having a calibrant chamber for containing the calibrant fluid and a sample chamber for containing the sample fluid;
- wherein the means for sequentially connecting mounts the multichamber reservoir for relative movement with respect to the inlet of the capillary passage;
- wherein the multichamber reservoir is a cylindrical reservoir having a generally vertical axis and having a generally vertical dividing wall for dividing an interior of the reservoir into the calibrant and sample chambers;
- wherein the means for sequentially connecting comprises means for rotatably mounting the reservoir for rotation about the generally vertical axis, and means for applying force to the reservoir to rotate the reservoir about the vertical axis to sequentially bring a lower end of the calibrant chamber and a lower end of the sample chamber into connection with the inlet of the capillary passage; and
- wherein the means for applying force comprises a cap for fitting over an upper end of the cylinder, the cap including means for engaging the dividing wall to transmit rotational force from the cap to the reservoir when the cap is rotated.

32. The sensing device of claim 31 and further comprising a rupturable top seal covering a top end of the calibrant chamber; and means for rupturing the top seal to expose the calibrant fluid to atmospheric pressure.

33. The sensing device of claim 32 wherein the cap has vent means for exposing sample fluid and body fluid within the chamber to atmospheric pressure.

34. The sensing device of claim 33 wherein the vent means comprises a vent hole in the cap positioned over each of the chambers.

35. The sensing device of claim 32 wherein the means for rupturing the seal at the top end is carried by the cap.

36. The sensing device of claim 31 wherein the means for engaging the dividing wall comprises first and second drive flanges extending generally downward from an interior surface of the cap for engaging opposite sides of the dividing wall to transmit rotational force from the cap to the cylinder when the cap is rotated.

37. The sensing device of claim 31 and further comprising means for defining a start position in which neither the calibrant chamber nor the sample chamber is aligned with the inlet, a calibrant test position in which the calibrant chamber is aligned with the inlet, and a sample test position in which the sample chamber is aligned with the inlet.

38. The sensing device of claim 37 and further comprising means for limiting rotation of the cylinder from the start position to a direction toward the calibrant test position.

39. The sensing device of claim 31 and further comprising:
- a rupturable bottom seal at a bottom end of each chamber; and
- a plow containing the inlet of the capillary passage for rupturing each bottom seal and extending into each chamber as rotation of the cylinder brings that chamber into alignment with the inlet.

40. A disposable single use sensing device for use with a clinical chemistry analyzer which determines a concentration of a selected chemical species in a sample fluid, the sensing device comprising:
- a multichamber reservoir having a sealed calibrant chamber for containing a calibrant fluid and a sample chamber for receiving the sample fluid;
- first rupturable seal means for sealing an end of the calibrant chamber;
- second rupturable seal means for sealing an end of the sample chamber;
- a capillary passage having an inlet, an outlet which is open to ambient air, a test chamber connected to the inlet, and a downstream channel connected between the test chamber and the outlet;
- sensing means for sensing concentration of the chemical species, the sensing means being positioned in the test chamber;
- mounting means for mounting the reservoir with respect to the inlet of the capillary passage to permit manual movement of the calibrant and sample chambers with respect to the inlet of the capillary passage from a start position in which neither chamber is connected to the inlet, to a first test position in which one of the chambers is connected to the inlet, and then to a second test position in which the other chamber is connected to the inlet to draw the fluid from one of the chambers and then the fluid from the other chamber into the capillary passage and into contact with the sensing means; and
- seal opening means for rupturing the first and second seal means.

41. The sensing device of claim 40 wherein the test chamber has a first circumference and the downstream channel has a second smaller circumference.

42. The sensing device of claim 41 wherein the capillary passage is S-shaped.

43. The sensing device of claim 40 wherein the reservoir is a cylinder having a generally vertical axis and a generally vertical dividing wall for dividing an interior of the reservoir into the calibrant and sample chambers, and wherein the mounting means rotatably mounts the reservoir for rotation about the vertical axis.

44. The sensing device of claim 43 and further comprising means for defining a start position in which neither the calibrant chamber nor the sample chamber is aligned with the inlet, a calibrant test position in which the calibrant chamber is aligned with the inlet, and a sample test position in which the sample chamber is aligned with the inlet.

45. The sensing device of claim 44 and further comprising means for limiting rotation of the reservoir from the start position to a direction toward the calibrant test position.

46. A sensing device comprising:
 a multichamber reservoir having a sealed calibrant chamber for containing a calibrant fluid and a sample chamber for receiving a sample fluid;
 a capillary passage having an inlet, an outlet, a test chamber connected to the inlet, and a downstream channel connected between the test chamber and the outlet;
 sensing means for sensing concentration of chemical species, the sensing means being positioned in the test chamber;
 mounting means for mounting the reservoir with respect to the inlet of the capillary passage to permit sequential connection of the calibrant and sample chambers with respect to the inlet of the capillary passage to draw the fluid from one of the chambers and then the fluid from the other chamber into the capillary passage and into contact with the sensing means;
 a rupturable bottom seal at a bottom end of each of the chambers; and
 a plow containing the inlet of the capillary passage for rupturing each bottom seal and extending into each chamber as relative movement brings that chamber into alignment with the inlet.

47. A sensing device comprising:
 a multichamber reservoir having a sealed calibrant chamber for containing a calibrant fluid and a sample chamber for receiving a sample fluid;
 a capillary passage having an inlet, an outlet, a test chamber connected to the inlet, and a downstream channel connected between the test chamber and the outlet;
 sensing means for sensing concentration of the chemical species, the sensing means being positioned in the test chamber; and
 mounting means for mounting the reservoir with respect to the inlet of the capillary passage to permit sequential connection of the calibrant and sample chambers with respect to the inlet of the capillary passage to draw the fluid from one of the chambers and then the fluid from the other chamber into the capillary passage and into contact with the sensing means; wherein the reservoir is a cylinder having a generally vertical axis and a generally vertical dividing wall for dividing an interior of the reservoir into the calibrant and sample chambers; wherein the mounting means rotatably mounts the reservoir for rotation about the vertical axis; wherein the mounting means includes a cylindrical guide sleeve; and wherein a lower end of the reservoir is rotatably mounted in the cylindrical guide sleeve.

48. The sensing device of claim 47 and further comprising a cap for fitting over an upper end of the cylinder, the cap including means for engaging the dividing wall to transmit rotational force from the cap to the cylinder when the cap is rotated.

49. A sensing device comprising:
 a multichamber reservoir having a sealed calibrant chamber for containing a calibrant fluid and a sample chamber for receiving a sample fluid;
 a capillary passage having an inlet, an outlet, a test chamber connected to the inlet, and a downstream channel connected between the test chamber and the outlet;
 sensing means for sensing concentration of the chemical species, the sensing means being positioned in the test chamber; and
 mounting means for mounting the reservoir with respect to the inlet of the capillary passage to permit sequential connection of the calibrant and sample chambers with respect to the inlet of the capillary passage to draw the fluid from one of the chambers and then the fluid from the other chamber into the capillary passage and into contact with the sensing means; wherein the reservoir is a cylinder having a generally vertical axis and a generally vertical dividing wall for dividing an interior of the reservoir into the calibrant and sample chambers; wherein the mounting means rotatably mounts the reservoir for rotation about the vertical axis; and wherein the cylinder has a vertical dividing wall for dividing an interior of the cylinder into the calibrant and sample chambers, and has a generally V-shaped bottom which includes a pair of inclined walls which are generally perpendicular to the dividing wall; and
 means for defining a start position in which neither the calibrant chamber nor the sample chamber is aligned with the inlet, a calibrant test position in which the calibrant chamber is aligned with the inlet, and a sample test position in which the sample chamber is aligned with the inlet.

50. The sensing device of claim 49 wherein the means for defining a start position, a calibrant test position and a sample test position comprises a plurality of circumferentially spaced detents.

51. A disposable single use sensing device for use with a clinical chemistry analyzer which determines a concentration of a selected chemical species in a sample fluid based upon sensor signals received at a receptacle, the sensing device comprising:
 a carrier;
 a multichamber reservoir having a calibrant chamber for containing a calibrant fluid and a sample chamber for containing the sample fluid;
 first seal means for sealing an end of the calibrant chamber;
 second seal means for sealing an end of the sample chamber;
 a capillary passage supported by the carrier and having an inlet, an outlet which is open to ambient air, a test chamber connected to the inlet, and a downstream channel connected between the test chamber and the outlet;
 sensing means for providing the sensor signals as a function of sensed concentration of the chemical species, the sensing means being positioned in the test chamber;
 mounting means for mounting the reservoir to permit manual movement of the calibrant and sample chambers with respect to the inlet of the capillary passage from a start position in which neither chamber is connected to the inlet, to a first test position in which one of the chambers is connected to the inlet, and then to a second test position in which the other chamber is connected to the inlet to draw the fluid from one of the chambers and then the fluid from the other chamber into the capillary passage and into contact with the sensing means; and means proximate the inlet for breaking the first and second seal means.

52. A method for determining a concentration of a selected chemical species in a sample fluid using a sensing device which includes a multichamber reservoir having a sealed calibrant chamber which contains a calibrant fluid and a sample chamber, a capillary passage having an inlet, an outlet, a test chamber connected to the inlet, and a downstream channel connected between the test chamber and the outlet, and a species selective sensor which exhibits a predetermined measurable characteristic which is a function of concentration of the selected chemical species, the method comprising:

placing sample fluid in the sample chamber;

moving the reservoir from a start position in which neither the calibrant chamber nor the sample chamber is connected to the inlet to a first test position in which a first seal is broken so that one of the calibrant and sample chambers is connected to the inlet to cause fluid from that chamber to be drawn into the test chamber;

measuring the predetermined measurable characteristic while the fluid from the one chamber is in the test chamber;

moving the reservoir from the first test position to a second test position in which a second seal is broken so that the other of the calibrant and sample chambers is connected to the inlet to cause the fluid from the other chamber to be drawn into the test chamber and purge the fluid from the one chamber from the test chamber into the downstream channel;

measuring the predetermined measurable characteristic while the fluid from the other chamber is in the test chamber; and deriving a concentration of the selected chemical species in the sample fluid based upon the predetermined measurable characteristic as measured when the calibrant fluid was in the test chamber and when the sample fluid was in the test chamber.

53. A disposable single use sensing device for use with a clinical chemistry analyzer which determines a concentration of a selected chemical species in a sample fluid based upon sensor signals, the sensing device comprising:

a carrier;

a calibrant chamber for containing a calibrant fluid, the calibrant chamber having a rupturable seal;

a sample chamber for containing the sample fluid, the sample chamber having a rupturable seal;

a capillary passage supported by the carrier and having an inlet, having an outlet which is open to ambient air, having a test chamber area located adjacent the inlet, and having a collection area located between the test chamber area and the outlet;

mounting means for movably mounting the calibrant and sample chambers with respect to the carrier and generally above the carrier and the inlet to permit sequential manual movement of the chambers with respect to the inlet of the capillary passage to draw the fluid from one of the chambers into the test chamber area and then to draw the fluid from the other chamber into the test chamber area while moving the fluid previously to the test chamber area into the collection area;

means for rupturing the seals of the calibrant and sample chamber; and sensing means for sensing concentration of the chemical species, the sensing means being positioned in communication with the test chamber area of capillary passage to provide sensor signals which are a function of sensed concentrations of the chemical species in the calibrant fluid and in the sample fluid.

54. A disposable single use sensing device for use with a clinical chemistry analyzer which determines a concentration of a selected chemical species, the sensing device comprising:

a multichamber reservoir having a sealed calibrant chamber for containing a calibrant fluid and a sample chamber for receiving the sample fluid;

a capillary passage having an inlet, an outlet which is open to ambient air, a test chamber connected to the inlet, and a downstream channel connected between the test chamber and the outlet;

sensing means for sensing concentration of the chemical species, the sensing means being positioned in the test chamber;

mounting means for rotatably mounting the reservoir with respect to the inlet of the capillary passage to permit manual rotation of the reservoir to cause sequential connection of the calibrant and sample chambers with respect to the inlet of the capillary passage to draw the fluid from one of the chambers and then the fluid from the other chamber into the capillary passage and into contact with the sensing means; and means proximate the inlet for rupturing a seal of the sealed calibrant chamber.

55. A disposable single use sensing device for use with a clinical chemistry analyzer which determines a concentration of a selected chemical species in a sample fluid based upon sensor signals, the sensing device comprising:

a carrier;

a multichamber reservoir having a calibrant chamber for containing a calibrant fluid and a sample chamber for containing the sample fluid;

a capillary passage supported by the carrier and having an inlet, an outlet which is open to ambient air, a test chamber connected to the inlet, and a downstream channel connected between the test chamber and the outlet, the inlet having a substantially smaller cross-sectional area than the test chamber so as to stop capillary flow when a rearward gas-liquid interface reaches the inlet;

sensing means for providing the sensor signals as a function of sensed concentration of the chemical species, the sensing means being positioned in the test chamber; and mounting means for mounting the reservoir generally above the carrier and the inlet to permit manual movement of the reservoir with respect to the carrier to cause sequential connection of the calibrant and sample chambers to the inlet of the capillary passage to draw the fluid from one of the chambers and then the fluid from the other chamber into the capillary passage and into contact with the sensing means.

* * * * *